United States Patent [19]

Kojima et al.

[11] Patent Number: 5,580,860
[45] Date of Patent: *Dec. 3, 1996

[54] PHARMACEUTICAL COMPOSITION CONTAINING 2-AMINO-6-CHLOROPURINE-9-β-D-2',3'-DIDEOXYRIBOFURANOXSIDE

[75] Inventors: Eiji Kojima; Hidetoshi Yoshioka; Kunichika Murakami, all of Iwakuni, Japan; Hiroaki Mitsuya; Takuma Shirasaka, both of Rockville, Md.; Samuel Broder, Bethesda, Md.

[73] Assignee: Sanyo Kokusaku Pulp Co., Ltd., Tokyo, Japan

[ * ] Notice: The term of this patent shall not extend beyond the expiration date of Pat. No. 5,053,499.

[21] Appl. No.: 446,155

[22] Filed: Dec. 5, 1989

[30] Foreign Application Priority Data

Sep. 29, 1989 [JP] Japan ..................... 1-254315

[51] Int. Cl.⁶ .......................... A61K 31/70; C07H 19/173
[52] U.S. Cl. .......................... 514/45; 536/27.14
[58] Field of Search ................ 536/24, 25, 27.14; 514/45, 46

[56] References Cited

U.S. PATENT DOCUMENTS 5,053,499 10/1991 Kojima et al. ............... 536/24

FOREIGN PATENT DOCUMENTS

| 206497 | 12/1986 | European Pat. Off. . |
| 286028 | 11/1987 | European Pat. Off. . |
| 286425 | 10/1988 | European Pat. Off. . |
| 285884 | 10/1988 | European Pat. Off. . |
| 0286425 | 10/1988 | European Pat. Off. . |

OTHER PUBLICATIONS

APP Environ Microbiol 55 (2) 419–24 (1989).
Chemical Pharmaceutical Bull 36 (10) 4153–6 (1988).
Synthesis (9) 670–4 (1988), Nucleic Acids Symposium Series 20 17 (1988).

J. AM. Chem. Soc., vol. 111, No. 22, Oct. 25, 1989, pp. 8502–8504, V. Nair, et al., "Novel, Stable Congeners of The Antiretroviral Compound 2',3'-Dideoxyadenosine" (cited Mar. 20, 1991).

J. Biolog. Chem., vol. 263, No. 12, Apr. 25, 1988, pp. 5870–5875, T. Haertle, et al., "Metabolism and Anti–Human Immuno–Deficiency Virus–1 Activity of 2–Halo–2', 3'–Dideoxyadenosine Derivatives* ".

J. Med. Chem., vol. 32, May 1989, pp. 1135–1140, A. Rosowsky, et al., "Synthesis of the 2–Chloro Analogues of 3'–Deoxy–Adenosine, 2', 3'–Dideoxyadenosine, and 2', 3'–Didehydro–2', 3'–Dideoxyadenosine as Potential Antiviral Agents".

Biochem. Biophys. Res. Commun., vol. 145, No. 1, May 29, 1987, pp. 277–283, J. Balzarini, et al., "The 2', 3'–Dideoxyriboside of 2,6–Diaminopurine and its 2', 3'–Didehydro Derivative Inhibit The Deamination of 2', 3'–Dideoxyadenosine, an . . . ".

Anticancer Research, vol. 7, Oct. 15–18, 1987, pp. 1023–1038, E. De Clercq, "Perspectives For The Chemotherapy of Aids".

Nair et al. (1989) J. Am. Chem. Soc., vol. 111, pp. 8502–8504.

*Primary Examiner*—Gary L. Kunz
*Attorney, Agent, or Firm*—Oblon, Spivak, McClelland, Maier, & Neustadt, P.C.

[57] ABSTRACT

An anti-AIDS virus agent is disclosed, which is characterized in that it contains the 2',3'-dideoxypurinenucleosides represented by the chemical formula (I):

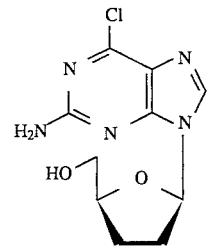

as an effective ingredient.

1 Claim, 3 Drawing Sheets

PHARMACEUTICAL COMPOSITION CONTAINING 2-AMINO-6-CHLOROPURINE-9-β-D-2',3'-DIDEOXYRIBOFURANOXSIDE

BACKGROUND OF THE INVENTION

The present invention relates to an anti-AIDS virus agent (anti-HIV agent) containing as an active agent 2-amino-6-chloropurine-9-β-D-2',3'-dideoxyribofuranoside and a therapeutic or preventive drug for AIDS containing said active agent.

Various anti-AIDS agents (anti-HIV agents) currently exist. Such agents include dideoxynucleosides such as azidothymidine (AZT), dideoxyadenosine (DDA) and dideoxyinosine (DDI). Dextran sulfate, soluble CD4, phosphonoformate, ribavirin, suramine, etc. are also known to be anti-AIDS virus agents (anti-HIV agents).

Since the anti-HIV property of AZT, DDA, DDI, etc., was recognized, new dideoxynucleosides modified with various substituents have been synthesized and proposed as new anti-HIV agents. Among these compounds, for example, are compounds having a halogen atom in the molecule, 6-chloropurine-9-β-D-2',3'-dideoxyribofuranoside and 6-iodopurine-9-β-D-2',3'-dideoxyribofuranoside (Japanese Unexamined Patent Publication No. Sho 63-267796). Moreover, 2-fluoro-2',3'-dideoxyadenosine and 2-bromo-2',3'-dideoxyadenosine are known (J. Biol. Chem., 263, 5870 (1988). Furthermore, 2-chloro-2',3'-dideoxyadenosine (J. Biol. Chem., 263, 5870 (1988); J. Med. Chem., 32, 1135 (1989) and 2-chloro-2',3'-didehydro-2',3'-dideoxyadenosine (J. Med. Chem., 32, 1135 (1989) are also known.

Similar compounds such as 9-(2-fluoro-2,3-dideoxy-β-D-threopentofuranosyl)-adenine etc. are also known (J. Med. Chem., 30, 2131 (1987).

Among the above compounds, however, the only one currently approved as a therapeutic drug for AIDS is AZT.

Most of the publicly-known anti-AIDS virus agents (anti-HIV agents) aforementioned have drawbacks including the points of the activity against AIDS virus (HIV), toxicity to cells, absorptivity into living bodies, etc. Moreover, with AZT being the only drug approved, side-effects such as myelotoxicty, etc. are known. Thus, additional anti-AIDS virus agents (anti-HIV agents) are currently a goal of the industry.

The purpose of the invention is to provide an anti-AIDS virus agent (anti-HIV agent) in order to solve the above problems.

The invention is based on the findings that 2-amino-6-chloropurine-9-β-D-2',3'-dideoxyribofuranoside has a high anti-AIDS virus activity and yet has a high absorptivity into cells.

SUMMARY OF THE INVENTION

This invention relates to an anti-AIDS virus agent containing as the active agents 2',3'-dideoxyribofuranoside, that is, 2-amino-6-chloropurine-9-β-D-2',3'-dideoxyribofuranoside represented by the chemical formula (I):

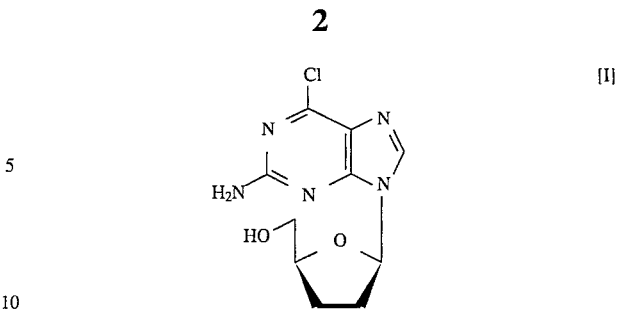

as an effective ingredient in the treatment of AIDS, HIV infection, and HIV-induced dementia in which this anti-AIDS virus agent (i.e., anti-AIDS virus agent containing 2-amino-6-chloropurine-9-β-D-2',3'-dideoxyribofuranoside) is used.

In the diagram, solid columns show the cells infected with HIV and open columns show those noninfected with HIV (control).

The ordinate shows the number of cells ($\times 10^5$) observed and the abscissa shows the concentration (μM) of anti-HIV agent 6-CL-DDG.

When the concentration of 6-CL-DDG was over 50 μM, DMSO (dimethyl sulfoxide) was added for improving the solubility. For example, in the case of 200 μM of 6-CL-DDG, DMSO was added in a concentration of 1%.

Figure 2:
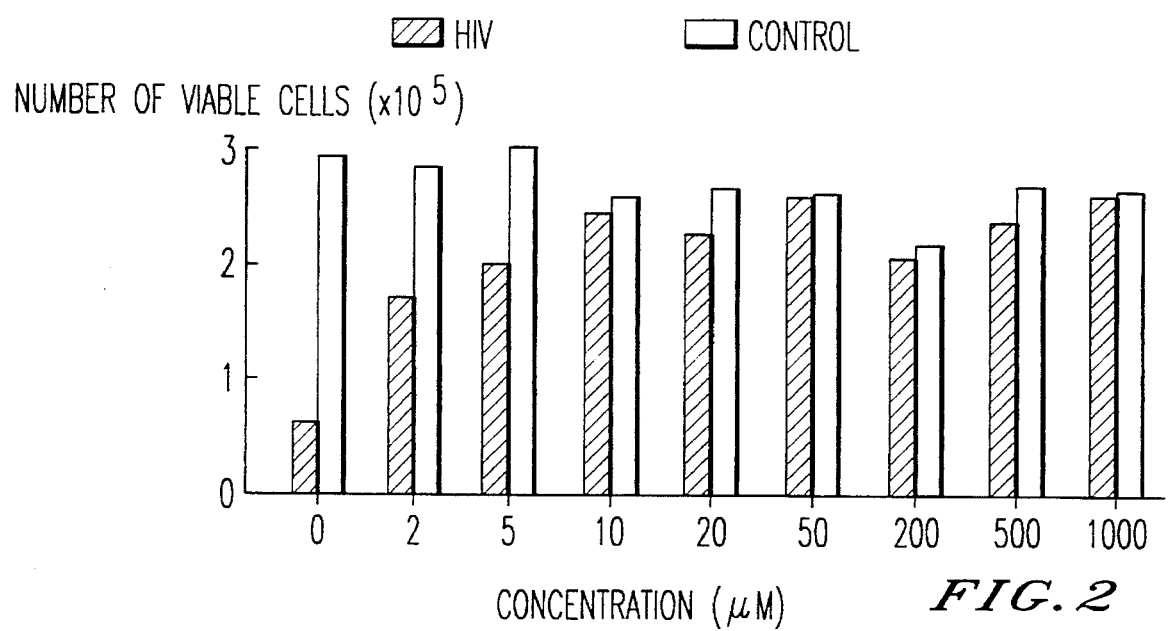

FIG. 2 is a diagram showing the results of an anti-HIV test of the comparative compound (DDG). In the diagram, solid columns show the cells infected with HIV and open columns show those noninfected with HIV (control). The ordinate shows the number of cells ($\times 10^5$) observed and the abscissa shows the concentration (μM) of anti-HIV agent (DDG).

Figure 3:
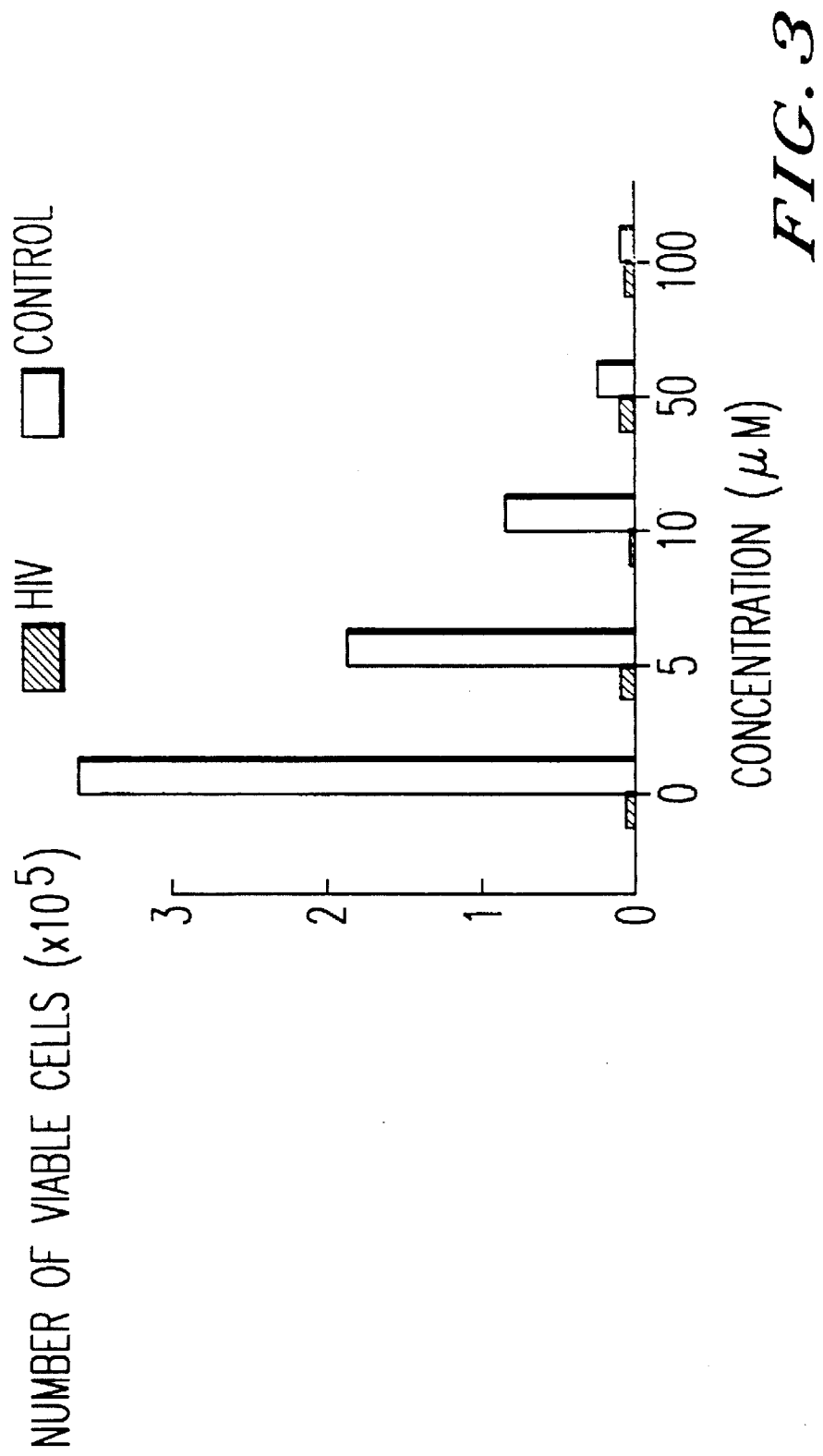

FIG. 3 is a diagram showing the results of an anti-HIV test of the comparative compound (2-chloro-2',3'-dideoxyadenosine; hereinafter abbreviated as 2-CL-DDA). In the diagram, solid columns show the cells infected with HIV and open columns show those noninfected with HIV (control). The ordinate shows the number of cells ($\times 10^5$) observed and the abscissa shows the concentration (μM) of comparative compound (2-CL-DDA).

Figure 4:
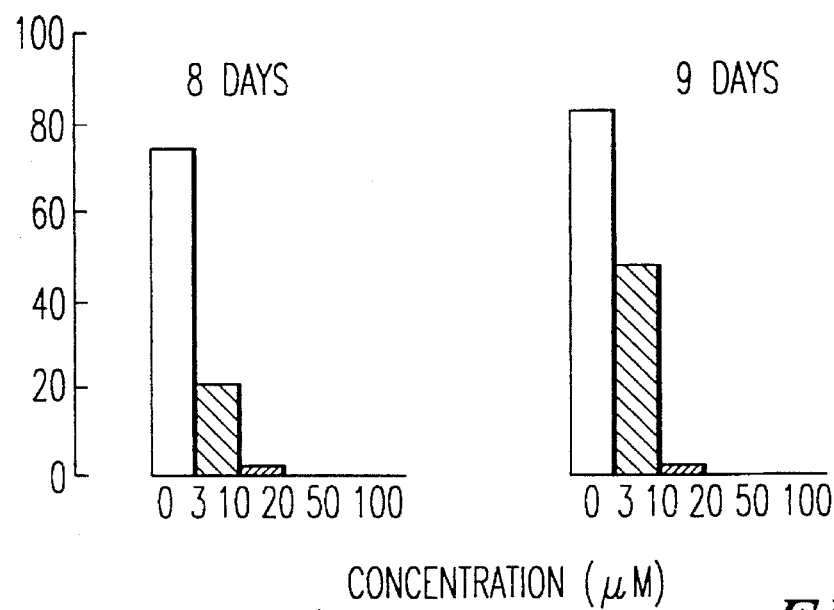

FIG. 4 is a diagram showing the results of an anti-HIV test of 6-CL-DDG. The left side shows the results on the 8th day and right side on the 9th day. The ordinate shows the rate (%) of H9 cells expressing the P24 antigen of HIV and the abscissa shows the concentration (μM) of 6-CL-DDG.

Figure 5:
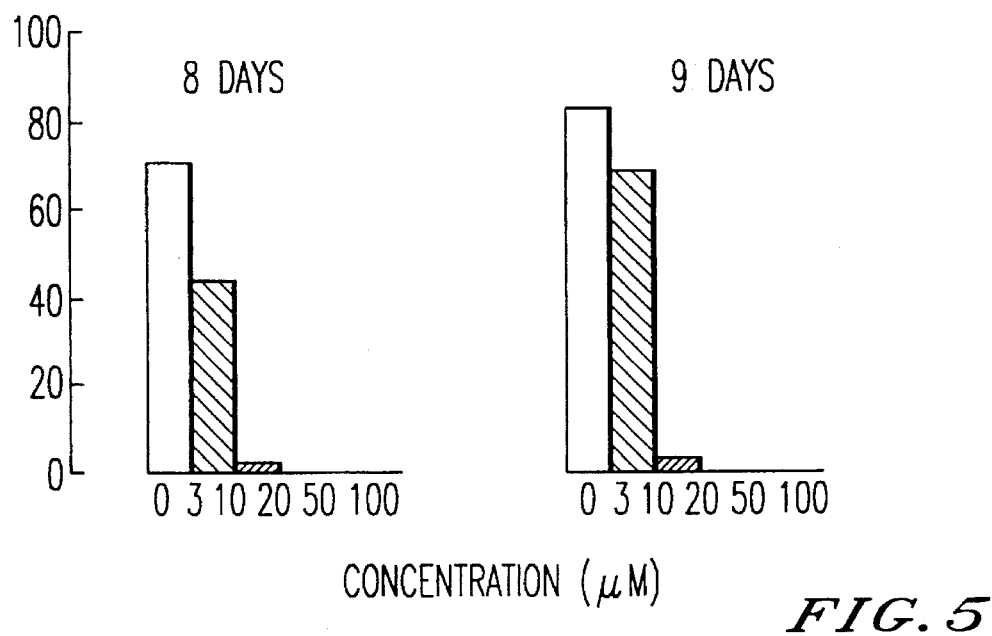

FIG. 5 is a diagram showing the results of an anti-HIV test of DDG. Left side shows the results on the 8th day and right side on the 9th day. The ordinate shows the rate (%) of H9 cells expressing the P24 antigen of HIV and the abscissa shows the concentration (μM) of DDG.

DETAILED DESCRIPTION OF THE INVENTION 2-amino-6-chloropurine-9-β-D-2',3'-dideoxyribofuranoside can be synthesized as followed:

By using 2',3'-dideoxyuridine and 2-amino-6-chloropurine as raw materials and by causing a base-exchange reaction (i.e., transglycosylation) between these through the action of microorganisms, corresponding 2-amino-6-chloropurine-9-β-D-2',3'-dideoxyribofuranoside can be obtained easily and in good yield (Japanese Patent Application No. Hei 1-46183).

Moreover, by using 2',3'-dideoxyuridine and 2-amino-6-chloropurine as raw materials and by causing the base-exchange reaction between these using immobilized microorganisms, corresponding 2-amino-6-chloropurine-9-β-D-2',3'-dideoxyribofuranoside can be continuously and simply synthesized in good yield (Japanese Patent Application No. Hei 1-181885).

Additionally, 2',3'-dideoxyribofuranosides having a halogen atom in the base portion are already known.

For example, in Japanese Unexamined Patent Publication No. Sho 63-267796, synthetic methods and others of two compounds of a) 6-chloropurine-9-β-D-2',3'-dideoxyribofuranoside and b) 6-iodopurine- 9-β-D-2',3'-dideoxyribofuranoside are disclosed In this report (Japanese Unexamined Patent Publication No. Sho. 63-267796), however, there are no descriptions about the data etc of anti-HIV activity or testing of these two compounds, thus it is difficult to presume immediately from this report whether or not the compounds a) and b) are useful as anti-HIV agents. Further, it is quite impossible to presume the anti-HIV property of 2',3'-dideoxyribofuranosides, the 6-position being halogenated, except in the compounds a) and b) from this report (Japanese Unexamined Patent Publication No. Sho 63-267796).

Moreover, in J. Biol. Chem., 263, 5870 (1988), there are descriptions about the anti-HIV effectiveness of three compounds; c) 2-fluoro-2',3'-dideoxyadenosine, d) 2-chloro-2',3'-dideoxyadenosine and e) 2-bromo-2',3'-dideoxyadenosine. According to these reports, however, while the compounds c), d) and e) exhibit HIV inhibition effect at a concentration of 1 to 10 μM, the cytotoxicity also appears from a concentration range of 1 to 10 μM. Thus, from the point of therapeutic coefficient (C=concentration to exhibit the cytotoxicity/concentration to inhibit HIV), these compounds (c, d and e) cannot be used practically as anti-HIV agents.

Further, in J. Med. Chem., 32, 1135 (1989), the anti-HIV effect of two compounds, d) 2-chloro-2',3'-dideoxyadenosine and f) 2-chloro-2',3'-didehydro-2',3'-dideoxyadenosine is described. According to this report, compound d) has no effect at all at a concentration of 2 μM and can barely inhibit 97% of the production of reverse transcriptase at a concentration of 100 μM. At the concentration of 100 μM, however, compound d exhibits cytotoxicity as high as 23%. Compound f) can inhibit 75% of the production of reverse transcriptase at a concentration of 20 μM. However, at a concentration over 20 μM, the toxicity is so strong that the test cannot be performed. Hence, in practice, the use of compounds d) and f) as anti-HIV agents is unreasonable.

Subsequently, among 2',3'-dideoxypurinenucleosides having a halogen atom in the base portion, compounds that are both effective against HIV and exhibit low toxicity to cells have not been found up to now.

As described above, in accordance with the invention, the ability of 2-amino-6-chloropurine-9-β-D-2',3'-dideoxyribofuranoside to have an extremely effective function as an anti-AIDS virus agent (anti-HIV agent) has been found for the first time.

Namely, in the invention, it has been found that 2-amino-6-chloropurine-9-β-D-2',3'-dideoxyribofuranoside has both high anti-AIDS virus effect (anti-HIV effect) and low cytotoxicity based on the structural characteristics. Further, in the invention, it has also been found that 2-amino-6-chloropurine-9-β-D-2',3'-dideoxyribofuranoside as an anti-AIDS virus agent (anti-HIV agent) has a high lipophilicity through the effect of the chlorine atom introduced to the 6-position of the purine base and, for this reason, it has an excellent permeability into cells in vivo.

The anti-HIV effect of 2-amino-6-chloropurine-9-β-D-2',3'-dideoxyribofuranoside of the invention will be explained.

Various compounds developed hitherto as anti-AIDS virus agents are described above. Each of them has its merits and demerits from the point of effect and toxicity, and thus many problems exist for their use in practice. Only azidothymidine (AZT) is approved now as an anti-AIDS virus agent and a therapeutic drug for AIDS.

AZT belongs to a group of compounds called 2',3'-dideoxynucleosides from the structure thereof, and, since it has no hydroxyl group at the 3'-position, it acts as a terminator of the DNA chain to stop directly the DNA synthesis of the AIDS virus. Moreover, since AZT is a very good substrate for reverse transcriptase of the AIDS virus, it acts antagonistically when the reverse transcriptase synthesizes DNA from AIDS virus RNA, to hinder the reverse transcriptase.

As described, since AZT is a compound directly acting against the reverse transcriptase, which is a key for the proliferation of AIDS virus, it has a high anti-HIV property and is a useful drug. However, negative side-effects, such as the occurrence of myelotoxicity etc. have been pointed out in vivo.

Drugs now under development as the next generation of therapeutic drugs for AIDS in place of AZT are, for example, DDC (2',3'-dideoxycytidine), DDA (2',3'-dideoxyadenosine), DDI (2',3'-dideoxyinosine). All of these have a similar structure to AZT and belong to a group of compounds called 2',3'-dideoxynucleosides.

DDC, DDA, and DDI all have a higher anti-HIV effect in vitro than that of AZT and currently clinical tests on these drugs are being conducted. Thus, these compounds are expected to be approved as drugs along with AZT.

However, as with AZT, side-effects such as disorder of peripheral nerves, myelotoxicity, etc. have been recently noted with these compounds. Thus, the development of better anti-HIV agents than those presently available are awaited.

Currently, one of the important symptoms of those infected with the AIDS virus (HIV) is a disorder of the brain.

In this phenomenon the AIDS virus reaches the brain of a person infected with HIV and destroys infectiously the cells of the brain to cause a certain dementia. In order to relax and treat this symptom due to HIV infection, it is necessary for the anti-HIV agent to pass more efficiently through the blood-brain barrier.

The passability of a drug through the blood-brain barrier is deeply related to the lipophilicity of the drug itself. The lipophilicity of DDC, DDA, and DDI aforementioned are rather lower (that is, the lipophilicity is poor) than AZT.

When developing a more effective anti-HIV agent, it is therefor clear that the affinity to cells represented by the lipophilicity should also be taken into account together with the high anti-HIV property and low cytotoxicity.

As a result of detailed investigations on how the lipophilicity can be raised while keeping both high anti-HIV activity and low cycotoxity in view of the reason described above, the inventors have found that 2-amino-6-chloropurine-9-β-D-2',3'-dideoxyribofuranaside concerned with the invention is consistent with this purpose.

Namely, 2-amino-6-chloropurine-9-β-D-2',3'-dideoxyribofuranoside of the invention has no hydroxyl group at 3'-position, thus it acts as a terminator of the DNA chain to hinder the reverse transcriptase of the AIDS virus (HIV). Moreover, by allowing a halogen atom to exist in the molecule, the inventors have succeeded in enhancing lipophilicity as compared with 2'3'-dideoxypurinenucleosides having no chlorine atom in the molecule. It will be easily known by analogy that, as a consequence, the passability through the blood-brain barrier becomes better. Further, by allowing the chlorine atom to locate at the 6-position of the purine base, the inventors have succeeded in achieving high anti-virus activity with low cytotoxicity.

EXAMPLE

The invention will be illustrated in more detail based on the example below.

Production Example 1

In a fermenter jar were placed 10 liters of liquid medium containing 5 g/L of yeast extract, 10 g/L of peptone and 5 g/L of NaCl and being adjusted to pH 7.0, which were pasteurized.

To this medium were inoculated 100 mg of *E. coli* JA-300 (Gene, 10, 157 (1980)), which were cultured under shaking for 16 hours at 37° C.

The fungus bodies were collected from the medium by centrifugal separation and, after being washed with physiological saline, these were suspended into 0.05M phosphate buffer (pH 7.5) adjusted with $KH_2PO_4$ and $Na_2HPO_4$ (100 mg wet/ml).

After being warmed to 50° C., 70 ml of said suspension of fungus bodies were added to 70 ml of reaction liquor which consisted of 0.05M phosphate buffer containing 7.0 mmol of 2',3'-dideoxyuridine and 7.0 mmol of 2-amino-6-chloro purine and being adjusted to pH 7.5 which $KH_2PO_4$ and $Na_2HPO_4$ and which were warmed beforehand to 50° C.

This was retained at 50° for 4 hours while shaking and then heated at 100° C. for 3 minutes.

After the completion of reaction, the fungus bodies were allowed to precipitate by centrifugal separation and the remaining supernatant was transferred to a beaker by the decantation method (supernatant 1).

To the fungus bodies being precipitated were added 70 ml of phosphate buffer (0.05M) with pH 7.5). After being stirred for some time, centrifugal separation procedure was carried out and the supernatant was transferred to a beaker by the decantation method. This procedure was repeated twice (supernatants 2 and 3).

Said supernatants 1, 2 and 3 were passed in sequence through a column (4×20 cm) packed with adsorptive resin (HP-20, made by Mitsubishi Kasei).

After the application of samples, this column was washed with 1 liter of distilled water and the product was eluted with methanol.

After eliminating the solvent, the product was dissolved again into chloroform containing 10% methanol, which was submitted to chromatography using a column (4×20 cm) packed with silica gel. For the mobile layer, chloroform containing 10% methanol was used.

The fractions containing the product were combined and concentrated, and the solids obtained were recrystallized from methanol. The crystals were dried to obtain 2-amino-6-chloropurine-9-β-D-2',3'-dideoxyribofuranoside (1.057 g, 3.92 mmol) (yield: 56%). Melting point: 138° C.

Test method
A-1 Antivirus test (1)

The anti-HIV effect of 2-amino-6-chloropurine-9-β-D-2',3'-dideoxyribofuranoside synthesized in the invention was assayed according to the method of Mitsuya et al (Biochemical Pharmacology, 36 2179 (1987)) using ATH8 cells (OKT4+T cell clone; Proc. Natl. Acad. Sci. U.S.A., 83, 1911 (1986)).

Namely, after pretreatment beforehand with polybrene (made by Sigma Co.), $2\times10^5$ ATH 8 cells were exposed to AIDS virus (HIV) for 45 minutes to infect (the number of HIV was made so as to be 2000 per ATH8 cell). Successively, the infected cells were suspended into every 1 ml of respective media containing interleukin 2 (IL-2) and being added with anti-HIV agent in various concentrations and into 1 ml of medium containing IL-2 alone and not containing anti-HIV agent at any rate.

These were cultured at 37° C. in a mixed gas comprising 5% carbon dioxide and 95% air.

The cells for reference were similarly prepared except allowing to infect with AIDS virus (HIV).

After 5 days, whole number of cells was counted by hemocytometer method based on the dyeing with trypan blue.

A-2 Antivirus test (2)

The anti-HIV effect of 6-Cl-DDG was assayed according to the method of Mitsuya et al (Proc. Natl. Acad. Sci. U.S.A. 83, 1911 (1986)) using H9 cell system. Namely, HIV-infected H9 cells added with anti-HIV agent in various concentrations were cultured for 8 days and 9 days, respectively, to assay the rate (%) of the target H9 cells expressing p24 gag protein of HIV. Measurement was made by a murine monoclonal antibody (M26) method.

B. Lipophilicity test

HIV infects not only the T4 cells, but also the cells of the central nervous system to cause dementia. It is known that most drugs cannot pass through the blood-brain barrier, but AZT passed through it relatively easily and has an effect also on dementia due to AIDS, to some extent.

In general, it is recognized that substances high in the lipophilicity are taken into the brain with relative ease and thereafter come out in the cerebrospinal fluid (J. Pharm. Pharmacol., 9, 345 (1957)). Hence, by determining the extent of lipophilicity, it is possible to presume the ease with which a compound passes through the blood-brain barrier (V International Conference on AIDS Abstracts, 559(1989)).

As a method for determining the extent of lipophilicity, it is a general rule to measure the partition coefficient (P) in water-n-octanol. Thus, the lipophilicity test of 2-amino-6-chloropurine-9-β-2',3'-dideoxyribofuranoside concerned with the invention was performed by the method of using partition coefficient P by shake-flask method (J. Pharm. Pharmacol., 39, 253 (1987)).

Namely, n-octanol and phosphate buffer (pH 7.4) were transferred into a separatory funnel and shaken for 3 hours with a shaker, which was then allowed to stand for 12 hours to separate respectively. Into 50 ml of n-octanol-saturated buffer thus obtained was dissolved 1 mg of sample (dried for 12 hours at 50° C. in a vacuum dryer) and 0.5 ml of this solution were taken as a sample for quantitative determination. Remaining 49.5 ml of n-octanol-saturated buffer and 49.5 ml of buffer-saturated n-octanol were transferred into a separatory funnel.

After shaking for 3 hours with a shaker, this was allowed to stand for 2 hours and then centrifuged (1500 rpm, 15 minutes). After gently removing the n-octanol layer, the sample for quantitative determination was taken. The quantitative determination was performed by the use of HPLC (refer to Table 1).

TABLE 1 conditions for quantitative determination

The quantitative determination of a sample was performed by using HPLC. The conditions for analysis were as follows:

| | |
|---|---|
| Column | TSK gel ODS - 80 TM |
| Eluent | Phosphate buffer (pH 6.9)/acetonitrile = 92/8 |
| Detection wavelength | UV 254 nm |
| Column temperature | 34.5° C. |
| Injection level | 10 μl |
| Standard sample concentration | 10, 20, 30 ppm |

Example 1

A-1 Anti-virus test (1)

Figure 1:
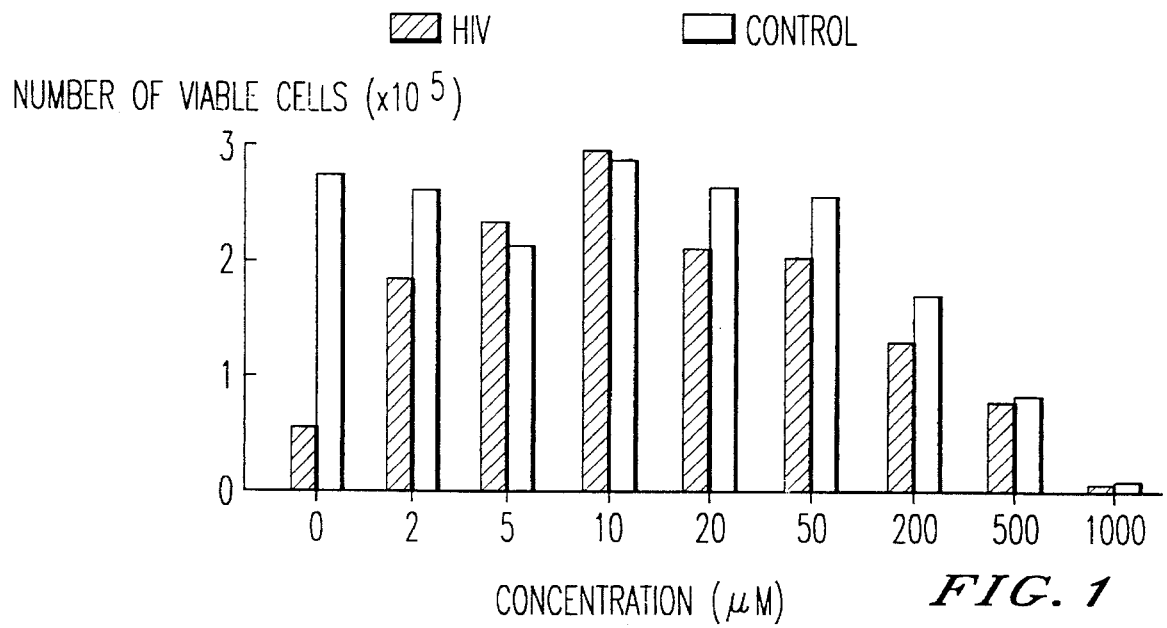
FIG. 1 is a diagram showing the results of an anti-HIV test of the compound (2-amino-6-chloropurine-9-β-D-2',3'-dideoxyribofuranoside, hereinafter abbreviated as 6-CL-DDG) of the invention.

Results of the anti-HIV test of 2-amino-6-chloropurine-2',3'-dideoxyribofuranoside are shown in FIG. 1.

This compound (6-Cl-DDG) exhibited HIV inhibition effect at a concentration of 2 μM and completely inhibited HIV at a concentration of 5 μM.

For comparison, the results of the anti-HIV test conducted using DDG (2'3'-dideoxyguanosine) (existing compound) are shown in FIG. 2. The complete inhibition concentration for HIV with DDG is a concentration of 10 μM.

From the results above, it can be seen that 6-Cl-DDG concerned with the invention has an equal or higher anti-HIV effect compared with DDG.

Besides, in the anti-HIV test of 6-Cl-DDG, DMSO (dimethyl sulfoxide) was added at concentrations over 50 μM in order to dissolve 6-Cl-DDG. When the concentrations of 6-Cl-DDG were 50 μM, 200 μM, 500 μM and 1000 μM, DMSO was added in amounts of 0.25%, 1% 2.5% and 5%, respectively.

Hence, the reason why the cytotoxicity appears over 200 μM in the anti-HIV test of 6-Cl-DDG is due to the influence of DMSO (Biochemical Pharmacology, 26, 2719 (1987)).

A-2 Antivirus test (2)

Results of the anti-HIV test of 6-Cl-DDG are shown in FIG. 4.

At a concentration of 3 μM, 6-Cl-DDG exhibits the inhibition effect on the expressing of p24 antigen and almost completely inhibits the expressing of p24 at 10 μM.

For comparison, the results of DDG determined under same conditions are shown in FIG. 5.

It can be seen also from these results that 6-Cl-DDG has an equal or higher anti-HIV effect compared with DDG.

B. Lipophilicity test

As described previously, with respect to the extent of lipophilicity, determination of partition coefficient P is general.

The partition coefficient P is defined as follows:
p=(Co - Cw)/Cw

Co: Concentration of sample in buffer before shaking
Cw: Concentration of sample in buffer after shaking Result of log P of 2-amino-6-chloropurine-2',3'-dideoxyribofuranoside is shown in Table 2. For comparison, results of log P of AZT (azidothymidine), DDI (dideoxyinosine) and DDG (dideoxyguanosine) are also put down.

From these results, it can be seen that the lipophilicity of AZT is higher compared with that of DDI or DDG and further the lipophilicity of 6-Cl-DDG of the invention is still higher than that of AZT.

And, a hypothetical relationship that, in the case of log P being between −1.5 and +0.7, the rate of passing through the blood-brain barrier (cerebrospinal fluid/plasma) also becomes higher with an increase in the value of log P is known (V International Conference on AIDS Abstracts), 559 (1989)).

Thus, according to this hypothesis, it is considered that, since 6-Cl-DDG concerned with the invention has better passability through the blood-brain barrier than AZT, DDI, DDG, etc. being known hitherto, it works on more effectively against HIV having invaded into the cells of central nervous system. For this reason, 6-Cl-DDG is considered to be particularly effective on the dementia disease etc. originating from AIDS.

TABLE 2

Log P of respective samples

| Sample | (Note 1) Elution time (min) | log P |
|---|---|---|
| 6-Cl-DDG | 16.3 | 0.30 |
| AZT | 19.1 | 0.12 |
| DDI | 4.7 | −1.22 |
| DDG | 4.7 | −1.06 |

(note 1)
The elution time is a time measured with HPLC (under the conditions shown in Table 1), during which repective samples eluted.

The invention provides an entirely new anti-HIV agent having concurrently three points of high anti-HIV activity, low cytotoxicity and good lipophilicity and having no precedent in the past and is a useful invention for the prevention and the therapy of AIDS and AIDS-related diseases. Moreover, it is an extremely useful invention also for the prevention and the therapy of central nervous disorder, dementia diseases, etc. caused through, in particular, the infection with HIV.

What is claimed is:

1. A pharmaceutical composition comprising, as an active ingredient, 2-amino-6-chloropurine-9-β-D-2',3'-dideoxyribofuranoside in a pharmaceutically acceptable carrier.

* * * * *